(12) United States Patent
Case et al.

(10) Patent No.: US 11,781,970 B2
(45) Date of Patent: Oct. 10, 2023

(54) DYNAMIC ADJUSTMENT OF COMPONENTS OF A DETECTION ASSEMBLY

(71) Applicant: Fenwal, Inc., Lake Zurich, IL (US)

(72) Inventors: Brian C. Case, Lake Villa, IL (US); Richard L. West, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 144 days.

(21) Appl. No.: 17/209,277

(22) Filed: Mar. 23, 2021

(65) Prior Publication Data

US 2021/0302304 A1 Sep. 30, 2021

Related U.S. Application Data

(60) Provisional application No. 62/994,492, filed on Mar. 25, 2020.

(51) Int. Cl.
*G01N 21/17* (2006.01)
*G01N 33/49* (2006.01)
(Continued)

(52) U.S. Cl.
CPC .............. *G01N 21/17* (2013.01); *G01N 33/49* (2013.01); *A61M 1/3693* (2013.01);
(Continued)

(58) Field of Classification Search
CPC ........ G01N 21/17; G01N 33/49; G01N 21/07; G01N 21/27; A61M 1/3693; A61M 2205/3306; A61M 2205/3375; A61M 2205/331; A61M 1/265; A61M 1/38; A61M 1/3621; B01D 63/16; B04B 13/00; B04B 2013/006
See application file for complete search history.

(56) References Cited

U.S. PATENT DOCUMENTS

| 5,194,145 A | 3/1993 | Schoendorfer |
| 5,316,667 A | 5/1994 | Brown et al. |

(Continued)

FOREIGN PATENT DOCUMENTS

| WO | WO 2018/053217 A1 | 3/2018 |
| WO | WO 2020/006549 A1 | 1/2020 |

OTHER PUBLICATIONS

Extended European Search Report for European Patent Application No. 21164127.9 dated Aug. 16, 2021.

*Primary Examiner* — Roy M Punnoose
(74) *Attorney, Agent, or Firm* — Cook Alex Ltd.

(57) ABSTRACT

A fluid processing device includes a detection assembly having a source and a detector. The source emits a signal to fluid or a fluid component in the fluid processing device, with at least a portion of the signal reaching the detector. The detection assembly further includes one or more adjustment systems configured to adjust the position and/or orientation of one or more components of the detection assembly. The position and/or orientation of the entire source and/or the entire detector, the position and/or orientation of a component of the source with respect to another component of the source, and/or the position and/or orientation of a component of the detector with respect to another component of the detector may be adjusted to increase the signal received by the detector.

20 Claims, 11 Drawing Sheets

(51) Int. Cl.
 *A61M 1/36* (2006.01)
 *B01D 63/16* (2006.01)
 *B04B 13/00* (2006.01)

(52) U.S. Cl.
 CPC .............. *A61M 2205/3306* (2013.01); *A61M 2205/3375* (2013.01); *B01D 63/16* (2013.01); *B04B 13/00* (2013.01); *B04B 2013/006* (2013.01)

(56) References Cited

U.S. PATENT DOCUMENTS

| | | | |
|---|---|---|---|
| 5,632,893 A | 5/1997 | Brown et al. | |
| 5,868,696 A | 2/1999 | Giesler et al. | |
| 7,422,693 B2* | 9/2008 | Carter | G01N 15/05 |
| | | | 210/512.1 |
| 8,075,468 B2 | 12/2011 | Min et al. | |
| 2005/0051466 A1* | 3/2005 | Carter | G01N 15/042 |
| | | | 210/512.1 |
| 2020/0072729 A1* | 3/2020 | Lumpkin | G01N 15/1425 |
| 2021/0172864 A1* | 6/2021 | McCurdy | A61B 5/14557 |

* cited by examiner

DYNAMIC ADJUSTMENT OF COMPONENTS OF A DETECTION ASSEMBLY

CROSS-REFERENCE TO RELATED APPLICATIONS

This application claims the benefit of and priority of U.S. Provisional Patent Application Ser. No. 62/994,492, filed Mar. 25, 2020, the contents of which are incorporated by reference herein.

BACKGROUND

Field of the Disclosure

The present disclosure relates to detection assemblies. More particularly, the present disclosure relates to dynamic adjustment of components of a detection assembly.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow circuit during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber.

It is known to employ an optical sensor assembly to monitor the flow of blood and/or blood components through the flow circuit in the centrifuge and determine various characteristics of the flow. For example, PCT Patent Application Publication No. WO 2018/053217 A1 (which is hereby incorporated herein by reference) relates to an optical sensor assembly for viewing into the centrifuge chamber for detecting and controlling the location of an interface between separated blood components. In this assembly, as in any other detection assembly, proper alignment of the various components of the detection assembly with respect to the subject being monitored is necessary to ensure that fluid is being properly monitored during a procedure. It may be the case that the fluid flow circuit is mounted to the hardware in a way that affects the performance of the detection assembly, such that it would be advantageous to enable dynamic adjustment of one or more components of the detection assembly in response to the orientation of a disposable circuit mounted to the hardware (or in response to some other factor) for improved performance.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing device includes a detection assembly having a source and a detector. The source is associated with a component of the fluid processing device, provided in an initial position and an initial orientation with respect to said component of the fluid processing device, and configured to emit a signal. The detector is associated with a structure of the fluid processing device, provided in an initial position and an initial orientation with respect to said structure of the fluid processing device, and configured to receive at least a portion of the signal. The detection assembly further includes an adjustment system associated with the source and/or an adjustment system associated with the detector. A controller of the fluid processing device is configured to control an adjustment system associated with the source to adjust the position and/or the orientation of the source with respect to said component of the fluid processing device and/or a position and/or an orientation of a component of the source with respect to another component of the source. The controller is configured to control an adjustment system associated with the detector to adjust the position and/or the orientation of the detector with respect to said structure of the fluid processing device and/or a position and/or an orientation of a component of the detector with respect to another component of the detector.

In another aspect, a method is provided for monitoring a fluid and/or a fluid component in a fluid processing device including a source and a detector, the source being associated with a component of the fluid processing device and provided in an initial position and an initial orientation with respect to said component of the fluid processing device, and the detector being associated with a structure of the fluid processing device and provided in an initial position and an initial orientation with respect to said structure of the fluid processing device. The method includes emitting a signal from the source and to a fluid and/or a fluid component in the fluid processing device, with at least a portion of the signal being received by the detector. The position and/or orientation of the source with respect to said component of the fluid processing device, the position and/or the orientation of the detector with respect to said structure of the fluid processing device, a position and/or an orientation of a component of the source with respect to another component of the source, and/or a position and/or an orientation of a component of the detector with respect to another component of the detector is adjusted.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-17 show components of a blood or fluid processing system that embodies various aspects of the present subject matter. While the system may be described herein in terms of its use in separating blood into two or more components, it should be understood that systems according to the present disclosure can be used for processing a variety of biological or bodily fluids (including fluids containing both bodily and non-bodily fluids, such as anticoagulated blood), as well as non-bodily fluids. Additionally, while an optical monitoring or detection assembly is described herein, it should be understood that the principles described herein (namely, the possibility of dynamically adjusting one or more components of a detection assembly) may be applied to other types of monitoring or detection assemblies, such as ultrasonic detection assemblies for detecting air in a fluid line.

Figure 1:
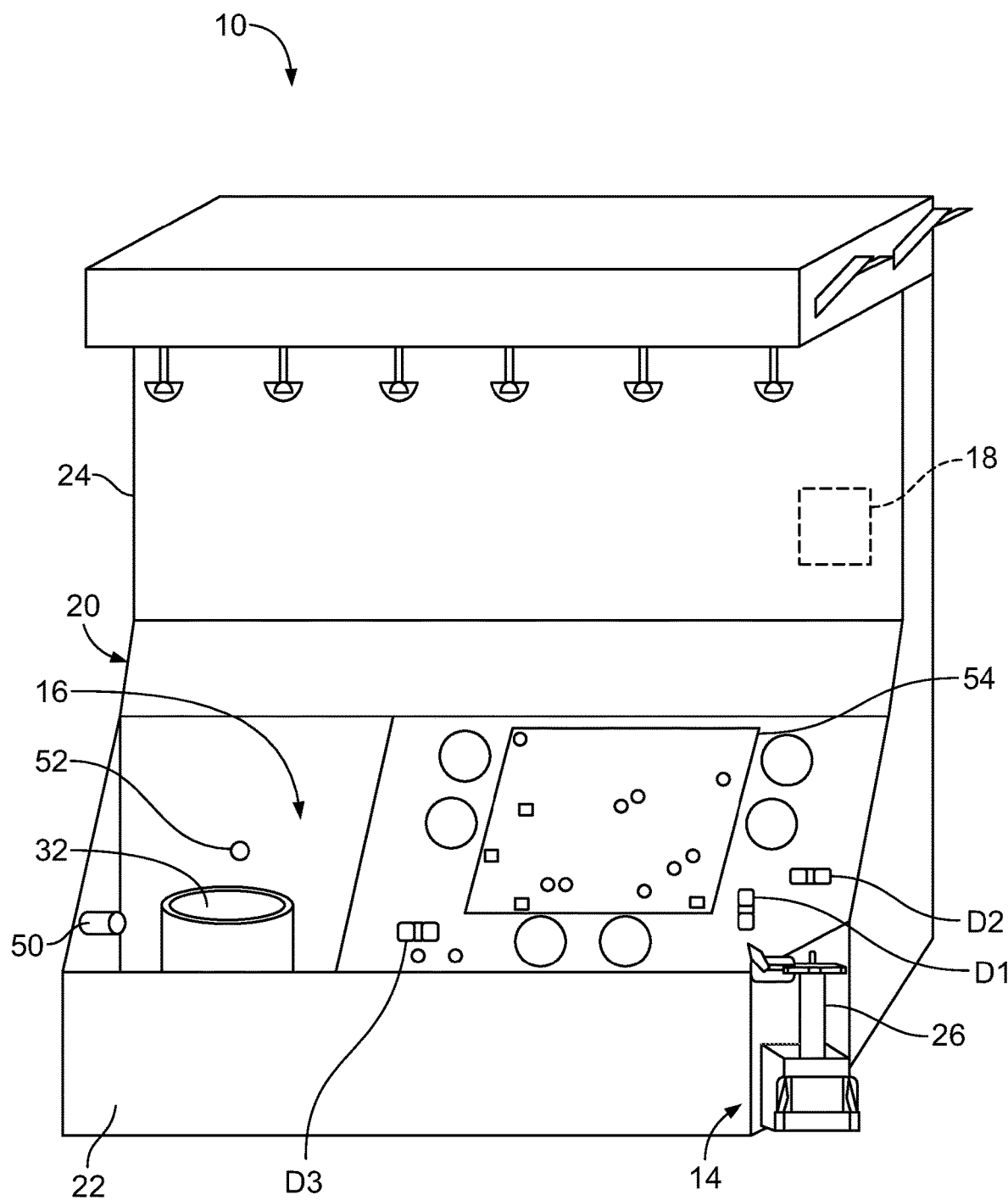
FIG. 1 is a perspective view of an exemplary fluid processing device that comprises a component of a fluid processing system according to an aspect of the present disclosure.
Figure 2:
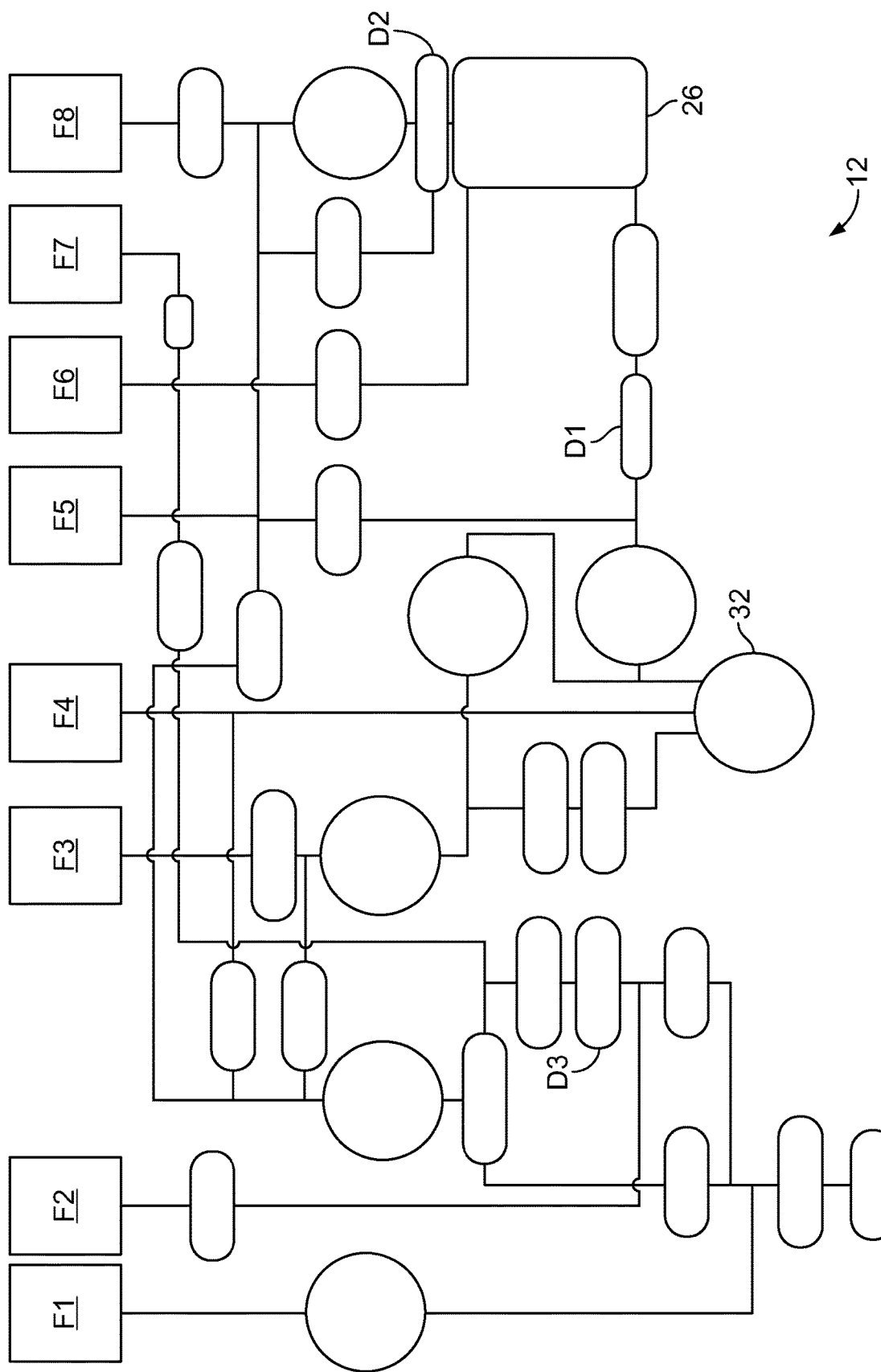
FIG. 2 is a schematic view of an exemplary disposable fluid flow circuit that may be mounted to the fluid processing device of FIG. 1 to complete a fluid processing system according to an aspect of the present disclosure.

Fluid processing systems according to the present disclosure typically include two principal components, a durable and reusable fluid processing device 10 (FIG. 1) and a disposable fluid flow circuit 12 (FIG. 2). While a disposable fluid flow circuit 12 may be advantageous for processing bodily fluids, it should be understood that the principles described herein are applicable to non-bodily fluids, in which case a disposable fluid flow circuit may be omitted.

The illustrated fluid processing device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the fluid processing device 10 (including a detection assembly) to perform a procedure selected by the operator. The principles described herein regarding dynamic adjustment of the components of a detection assembly are not limited to any particular fluid processing systems or procedures, so no complete fluid processing devices or procedures will be described in detail herein. However, reference may be made to PCT Patent Application Publication No. WO 2018/053217 A1 for a detailed description of the fluid processing device 10 of FIG. 1, along with various exemplary procedures that may be carried out using such a system.

I. The Durable Fluid Processing Device

The fluid processing device 10 (FIG. 1) is configured as a durable item that is capable of long-term use. It should be understood that the fluid processing device 10 of FIG. 1 is merely exemplary of one possible configuration and that fluid processing devices according to the present disclosure may be differently configured. For example, it is within the scope of the present disclosure for the fluid processing device to omit either or both of a spinning membrane separator drive unit 14 and a centrifugal separator 16 and to instead process fluid without separating it.

In the illustrated embodiment, the fluid processing device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24.

A. Spinning Membrane Separator Drive Unit

The illustrated fluid processing device 10 includes a spinner support or spinning membrane separator drive unit 14 (FIG. 1) for accommodating a generally cylindrical spinning membrane separator 26 of a fluid flow circuit 12 (FIG. 2). U.S. Pat. No. 5,194,145 (which is hereby incorporated herein by reference) describes an exemplary spinning membrane separator drive unit that would be suitable for incorporation into the fluid processing device 10, but it should be understood that the spinning membrane separator drive unit 14 may be differently configured without departing from the scope of the present disclosure. The principles described herein regarding adjustment of the components of a detection assembly may be practiced in combination with any configuration of a spinning membrane separator or in the absence of a spinning membrane separator, so the spinning membrane separator drive unit 14 is not described in detail herein.

B. Centrifugal Separator

Adjustment of the components of a detection assembly are described herein in the context of a detection assembly of the centrifugal separator 16. Accordingly, a particularly configured centrifugal separator 16 and associated centrifugal separation chamber 32 and detection assembly will be described herein for illustrative purposes. However, it should be understood that such principles may be practiced in combination with any configuration of a centrifugal separator 16 or in the absence of a centrifugal separator.

Figure 3:
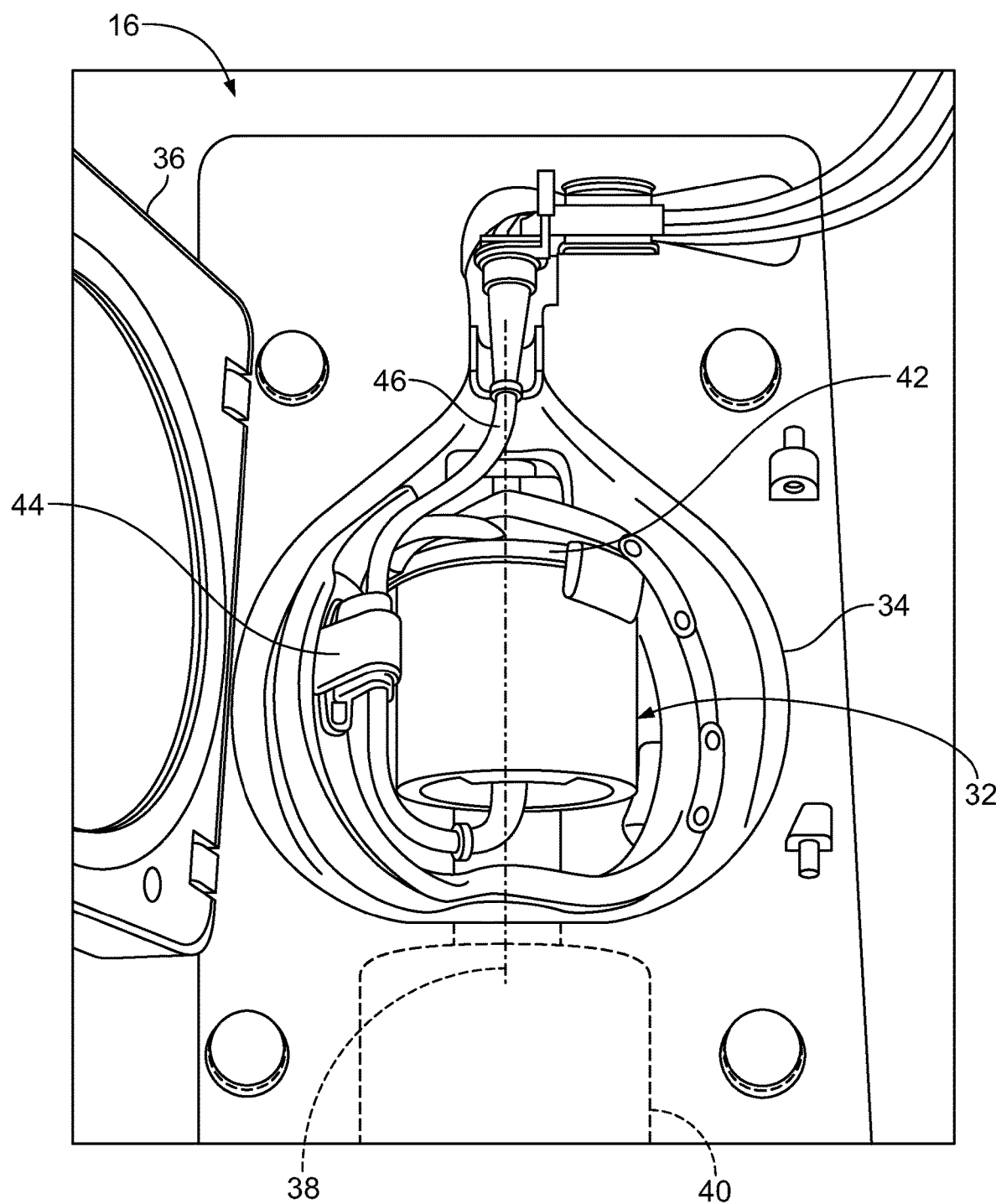
FIG. 3 is a perspective view of an exemplary centrifugal separator of the fluid processing device of FIG. 1, with the centrifugal separation chamber of a fluid flow circuit mounted therein.

The illustrated centrifugal separator 16 includes a centrifuge compartment 34 that may receive the other components of the centrifugal separator 16 (FIG. 3). The centrifuge compartment 34 may include a lid 36 that is opened to insert and remove a centrifugal separation chamber 32 of the fluid flow circuit 12. During a separation procedure, the lid 36 may be closed with the centrifugal separation chamber 32 positioned within the centrifuge compartment 34, as the centrifugal separation chamber 32 is spun or rotated about an axis 38 under the power of an electric drive motor or rotor 40 of the centrifugal separator 16.

Figure 4:
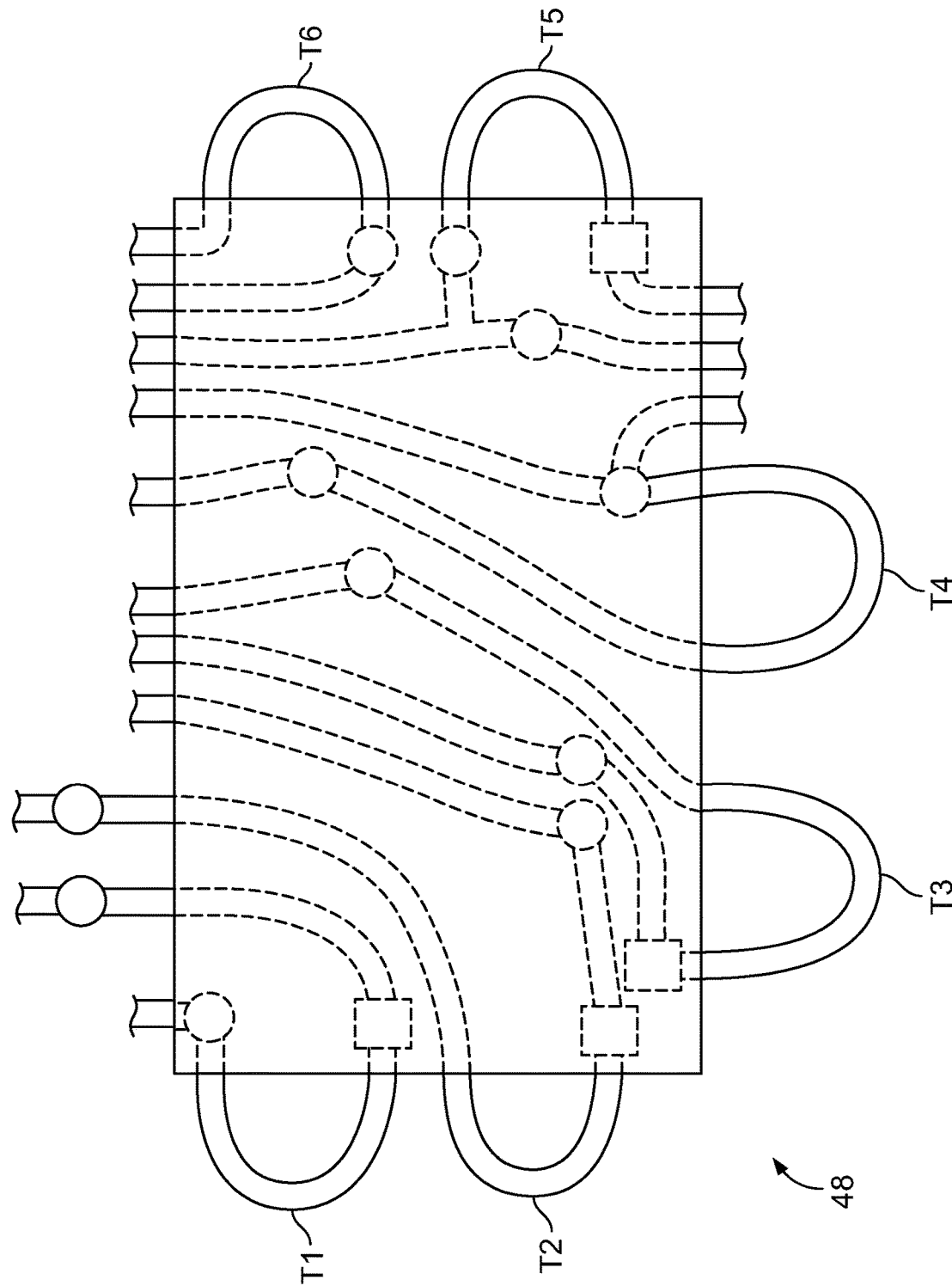
FIG. 4 is a top plan view of an exemplary cassette of a fluid flow circuit, which can be actuated to perform a variety of different fluid processing procedures in association with the fluid processing device shown in FIG. 1.

The particular configuration and operation of the centrifugal separator 16 depends upon the particular configuration of the centrifugal separation chamber 32 of the fluid flow circuit 12. In one embodiment, the centrifugal separator 16 is similar in structure and operation to that of the ALYX system manufactured by Fenwal, Inc. of Lake Zurich, Ill., which is an affiliate of Fresenius Kabi AG of Bad Homburg, Germany, as described in greater detail in U.S. Pat. No. 8,075,468, which is hereby incorporated herein by reference. More particularly, the centrifugal separator 16 may include a carriage or support 42 that holds the centrifugal separation chamber 32 and a yoke member 44. The yoke member 44 engages an umbilicus 46 of the fluid flow circuit 12, which extends between the centrifugal separation chamber 32 and a cassette 48 of the fluid flow circuit 12 (FIG. 4). The yoke member 44 causes the umbilicus 46 to orbit around the centrifugal separation chamber 32 at a one omega rotational speed. The umbilicus 46 twists about its own axis as it orbits around the centrifugal separation chamber 32. The twisting of the umbilicus 46 about its axis as it rotates at one omega with the yoke member 44 imparts a two omega rotation to the centrifugal separation chamber 32, according to known design. The relative rotation of the yoke member 44 at a one omega rotational speed and the centrifugal separation chamber 32 at a two omega rotational speed keeps the umbilicus 46 untwisted, avoiding the need for rotating seals.

Figure 6:
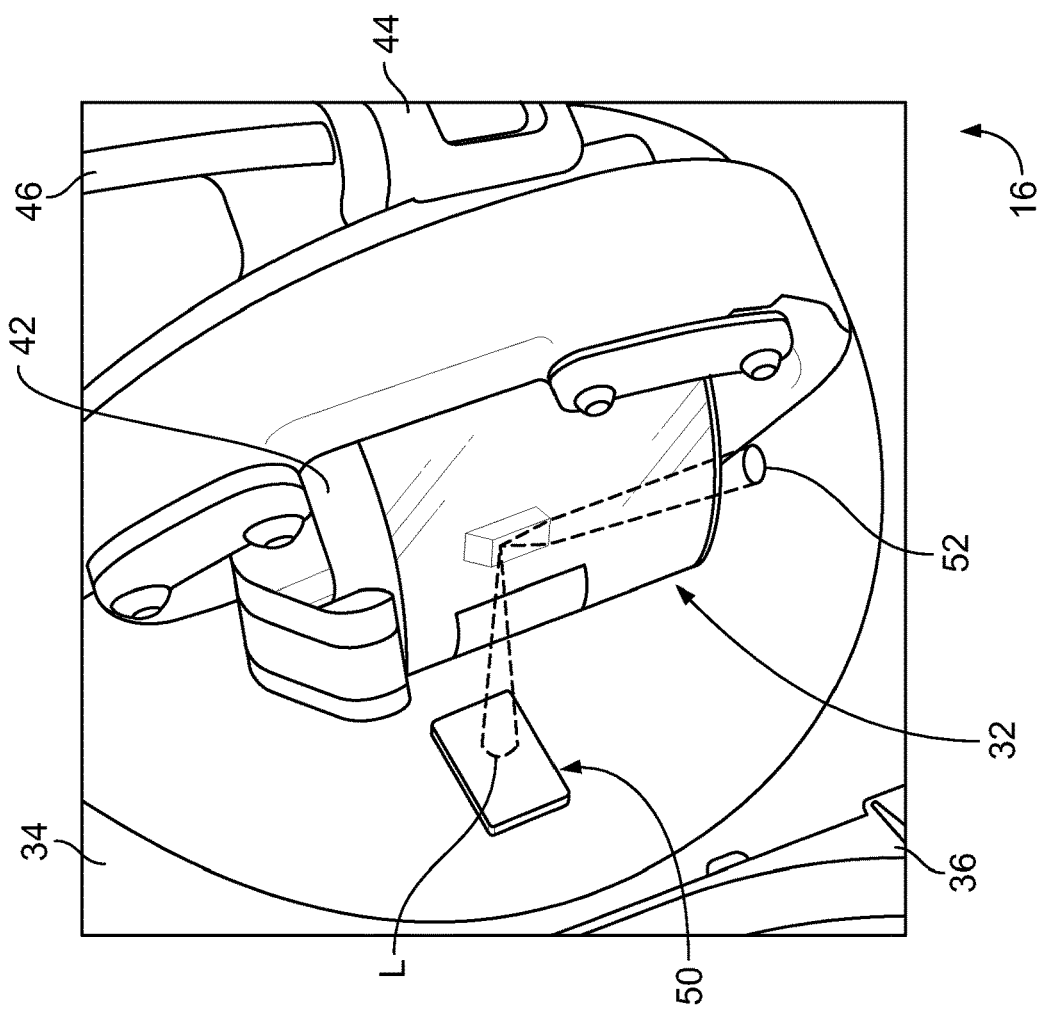
FIG. 6 is a perspective view of the centrifugal separator of FIG. 3, with the light source operating to transmit a light beam to a light detector of the interface monitoring assembly.
Figure 5:
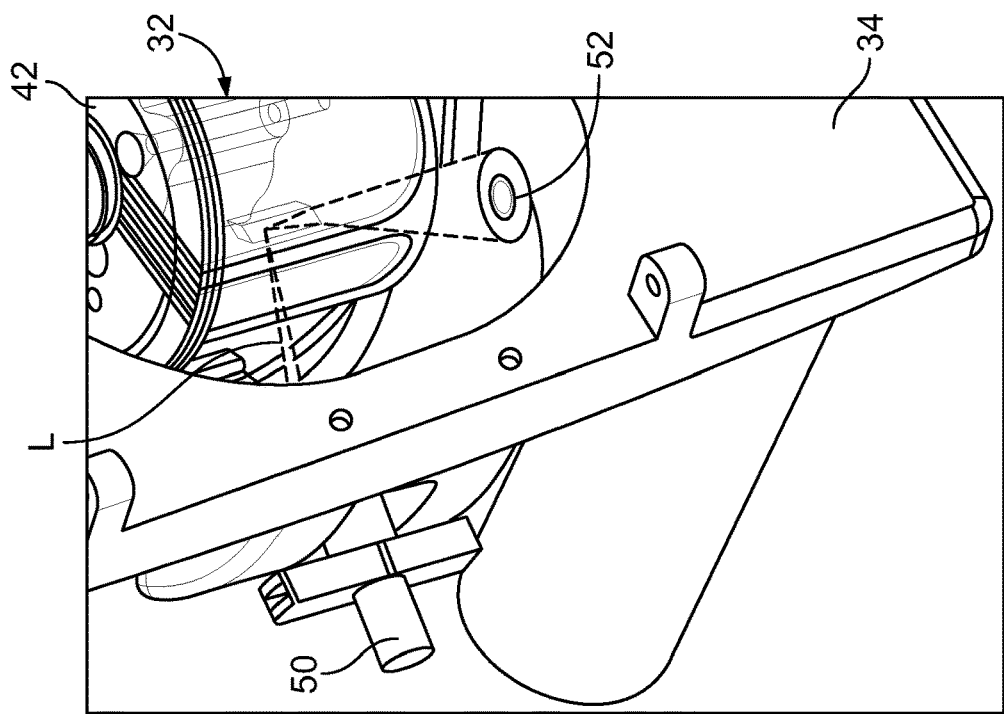
FIG. 5 is a perspective view of the centrifugal separator of FIG. 3, with selected portions thereof broken away to show a light source of an interface monitoring assembly.
Figure 7:
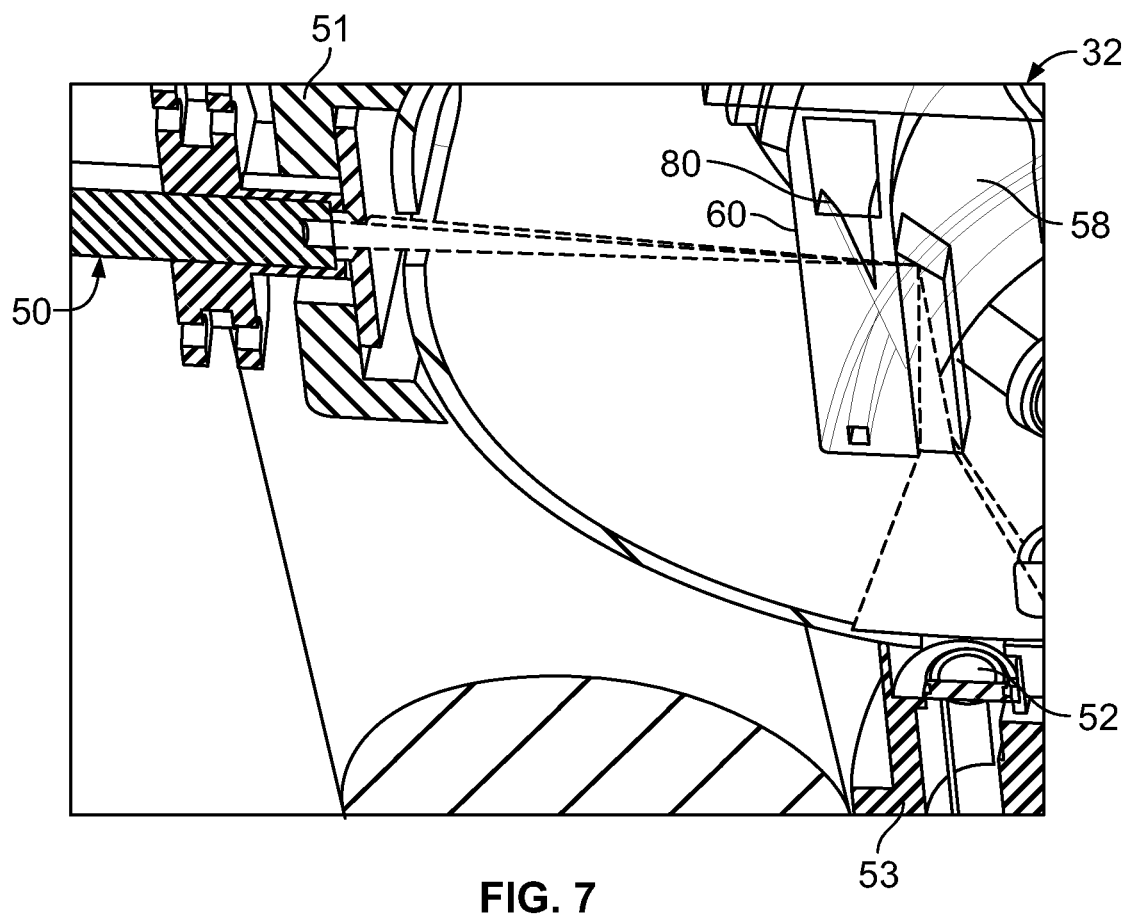
FIG. 7 is a perspective view of the centrifugal separator of FIG. 3, with selected portions thereof broken away to show the light source and light detector of the interface monitoring assembly.

A fluid is introduced into the centrifugal separation chamber 32 by the umbilicus 46, with the fluid being separated (e.g., into a layer of less dense components, such as platelet-rich plasma, if the fluid is blood, and a layer of more dense components, such as packed red blood cells, if the fluid is blood) within the centrifugal separation chamber 32 as a result of centrifugal forces as it rotates. Components of an interface monitoring assembly may be positioned within the centrifuge compartment 16 to oversee separation of fluid within the centrifugal separation chamber 32. As shown in FIGS. 5-7, the interface monitoring assembly may include a light source 50 and a light detector 52, which is positioned and oriented to receive at least a portion of the light emitted by the light source 50. The illustrated light source 50 is associated with a stationary component 51 of the centrifuge compartment 34 and the illustrated light detector 52 are is associated with a stationary structure 53 of the centrifuge compartment 34, but either or both may instead be associated with a movable structure or component of the fluid processing device 10, as in U.S. Pat. No. 5,316,667, which is hereby incorporated herein by reference. Further, as will be described in greater detail herein, the position and/or orientation of the light source 50 and/or the light detector 52 may be adjusted with respect to the structure or component of the fluid processing device 10 with which it is associated according to an aspect of the present disclosure.

The initial or default orientation and position of the various components of the interface monitoring assembly depend at least in part on the particular configuration of the centrifugal separation chamber 32. In general, though, the light source 50 emits a light beam "L" (e.g., a laser light beam) through the separated fluid components within the centrifugal separation chamber 32 (which may be formed of a material that substantially transmits the light L or at least a particular wavelength of the light L without absorbing it). A portion of the light L reaches the light detector 52, which transmits a signal to the controller 18 that is indicative of the location of an interface between the separated fluid components. If the controller 18 determines that the interface is in the wrong location (which can affect the separation efficiency of the centrifugal separator 16 and/or the quality of the separated blood components), then it can issue commands to the appropriate components of the fluid processing device 10 to modify their operation so as to move the interface to the proper location.

C. Other Components of the Fluid Processing Device

In addition to the spinning membrane separator drive unit 14 and the centrifugal separator 16, the fluid processing device 10 may include other components compactly arranged to aid fluid processing. Exemplary components (including a pump system, a cassette station 54 to accommodate the cassette 48 of the fluid flow circuit 12) are described in greater detail in PCT Patent Application Publication No. WO 2018/053217 A1.

Among the various components of the fluid processing device 10 are a plurality of detection assemblies D1-D3. While the adjustment principles described herein are presented with reference to the interface monitoring assembly of the centrifugal separator 16, it should be understood that similar principles may be applied to the other detection assemblies D1-D3, as well as detection assemblies that are differently configured from the ones described herein.

One of the detection assemblies comprises a centrifuge outlet sensor D1 for determining one or more properties of fluids flowing out of the centrifugal separator 16. If the fluid flowing out of the centrifugal separator 16 includes red blood cells, the centrifuge outlet sensor D1 may be configured to determine the hematocrit of the fluid. If the fluid flowing out of the centrifugal separator 16 is platelet-rich plasma, the centrifuge outlet sensor D1 may be configured to determine the platelet concentration of the platelet-rich plasma. The centrifuge outlet sensor D1 may detect the one or more properties of a fluid by optically monitoring the fluid as it flows through tubing of the fluid flow circuit 12 or by any other suitable approach. The controller 18 may receive signals from the centrifuge outlet sensor D1 that are indicative of the one or more properties of fluid flowing out of the centrifugal separator 16 and use the signals to optimize the procedure based upon that property or properties.

Another one of the detection assemblies comprises a spinner outlet sensor D2, which accommodates tubing of a fluid flow circuit 12 that flows a separated fluid component out of a spinning membrane separator 26 of the fluid flow circuit 12.

A third one of the detection assemblies comprises an air detector D3 (e.g., an ultrasonic bubble detector), which accommodates tubing of the fluid flow circuit 12 that flows fluid to a recipient. It may be advantageous to prevent air from reaching the recipient, so the air detector D3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

D. Controller

As described above, the fluid processing device 10 includes a controller 18, which is suitably configured and/or programmed to control operation of the fluid processing device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid processing device 10.

The controller 18 is configured and/or programmed to execute at least one fluid processing application but, more advantageously, is configured and/or programmed to execute a variety of different fluid processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and a mononuclear cell collection procedure. Additional or alternative procedure applications (e.g., plasma exchange, red blood cell exchange, and photopheresis) can be included without departing from the scope of the present disclosure.

More particularly, in carrying out any one of these fluid processing applications, the controller 18 is configured and/or programmed to control one or more of the following tasks: drawing fluid into a fluid flow circuit 12 mounted to the fluid processing device 10, conveying fluid through the fluid flow circuit 12 to a location for separation (i.e., into the spinning membrane separator 26 or the centrifugal separation chamber 32 of the fluid flow circuit 12), separating the fluid into two or more components as desired, and conveying the separated components into storage containers, to a second location for further separation (e.g., into whichever of the spinning membrane separator 26 and centrifugal separation chamber 32 that was not used in the initial separation stage), or to a recipient (which may be the source from which the fluid was originally drawn).

This may include instructing the spinning membrane separator drive unit 14 and/or the centrifugal separator 16 to operate at a particular rotational speed and instructing a pump to convey fluid through a portion of the fluid flow circuit 12 at a particular flow rate. Hence, while it may be described herein that a particular component of the fluid processing device 10 (e.g., the spinning membrane separator drive unit 14 or the centrifugal separator 16) performs a particular function, it should be understood that that component is being controlled by the controller 18 to perform that function.

Before, during, and after a procedure, the controller 18 may receive signals from various components of the fluid processing device 10 to monitor various aspects of the operation of the fluid processing device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring assembly and the centrifuge outlet sensor D1. The signals that the controller 18 receives from the light detector 52 are indicative of the location of an interface between the separated fluid components within the centrifugal separation chamber 32, while the signals from the centrifuge outlet sensor D1 indicate whether the target interface location should be adjusted. If the controller 18 determines that the interface is in the wrong location, then it can issue commands to the appropriate components of the fluid processing device 10 to modify their operation so as to move the interface to the proper location. For example, the controller 18 may instruct a pump to cause blood to flow into the centrifugal separation chamber 32 at a different rate and/or for a separated fluid component to be removed from the centrifugal separation chamber 32 at a different rate and/or for the centrifugal separation chamber 32 to be spun at a different speed by the centrifugal separator 16.

As will be described in greater detail, if the controller 18 determines that the performance of a detection assembly would be improved by adjusting one or more components of that detection assembly, the controller 18 may issue commands to adjust such component(s), as appropriate.

II. The Disposable Fluid Flow Circuit

A. Overview

As for the fluid flow circuit or flow set 12 (FIG. 2), it is intended to be a sterile, single use, disposable item. Before beginning a given procedure, the operator loads various components of the fluid flow circuit 12 in the case 20 in association with the fluid processing device 10. Proper operation of the various detection assemblies of the fluid processing device 10 may depend upon proper orientation of the fluid flow circuit 12 with respect to the detection assemblies, such that care should be taken when mounting the fluid flow circuit 12 to the fluid processing device 10. However, in the event that one or more of the components of the fluid flow circuit 12 is not properly oriented with respect to an associated detection assembly of the fluid processing device 10, one or more of the components of that detection assembly may be adjusted to improve performance of the detection assembly. While improper installation or misalignment of a fluid flow circuit 12 may be a common reason for adjusting a component of a detection assembly, it should be understood that other reasons exist, such that the principles described herein are not limited to use in fluid processing systems employing a disposable fluid flow circuit.

Once the fluid flow circuit 12 is mounted to the fluid processing device 10, the controller 18 implements a procedure based upon preset protocols, taking into account other input from the operator. Upon completing the procedure, the operator removes the fluid flow circuit 12 from association with the fluid processing device 10. The portions of the fluid flow circuit 12 holding the collected fluid component or components (e.g., collection containers or bags) are removed from the case 20 and retained for storage, immediate use, or further processing. The remainder of the fluid flow circuit 12 is removed from the case 20 and discarded.

A variety of different disposable fluid flow circuits may be used in combination with the fluid processing device 10, with the appropriate fluid flow circuit depending on the procedure to be carried out using the system. Generally speaking, though, the fluid flow circuit 12 includes a cassette 48 (FIG. 4) to which the other components of the fluid flow circuit 12 are connected by flexible tubing. In one embodiment, the cassette 48 is similarly configured to the cassette of U.S. Pat. No. 5,868,696 (which is hereby incorporated herein by reference), but is adapted to include additional components (e.g., more tubing loops T1-T6) and functionality.

The other components may include a plurality of fluid containers F1-F8 (for holding fluid to be processed, a separated fluid component, an intravenous fluid, or an additive solution, for example), one or more fluid source access devices (e.g., a connector for accessing fluid within a fluid container), and a spinning membrane separator 26 and/or a centrifugal separation chamber 32 (FIG. 2).

B. Centrifugal Separation Chamber

Figure 8:
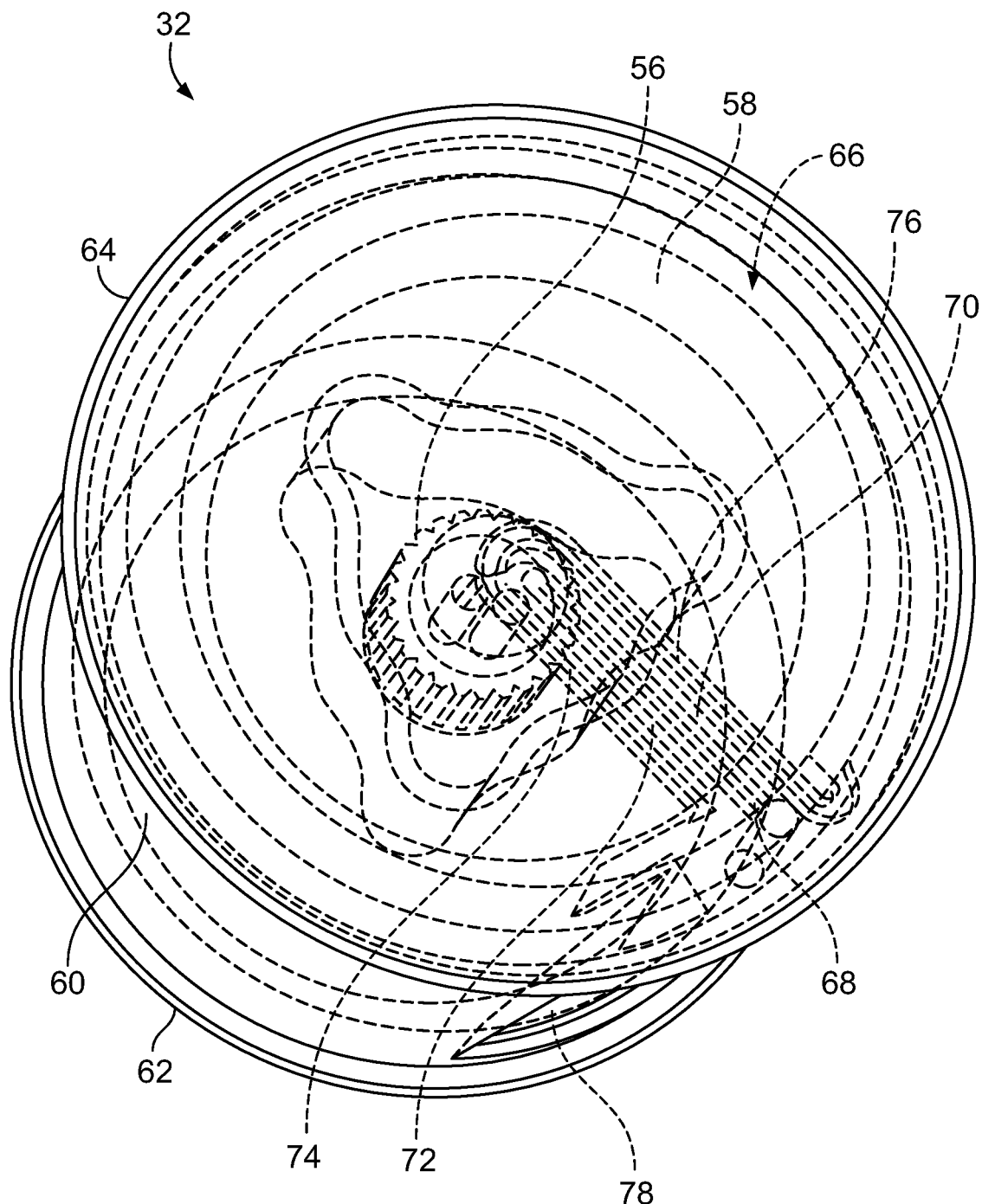
FIG. 8 is a perspective view of an exemplary centrifugal separation chamber of a fluid flow circuit.
Figure 9:
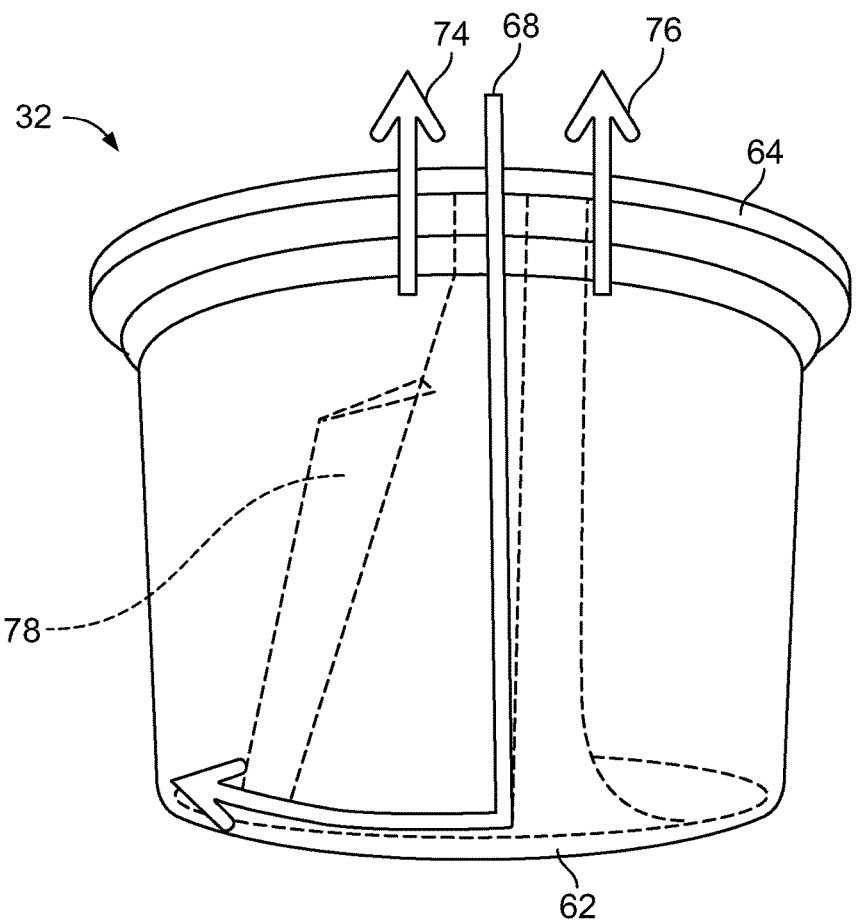
FIG. 9 is a front elevational view of the centrifugal separation chamber of FIG. 8.
Figure 10:
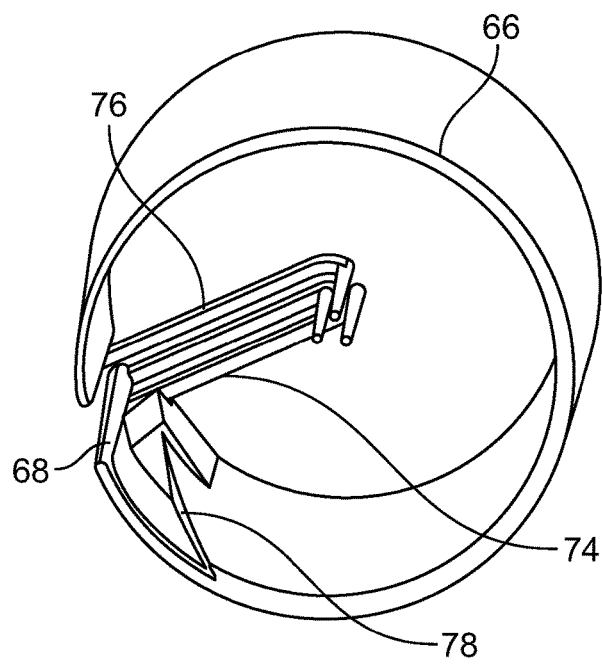
FIG. 10 is a bottom perspective view of the fluid flow path through the centrifugal separation chamber of FIG. 8.

An exemplary centrifugal separation chamber 32 is shown in FIGS. 8 and 9, while FIG. 10 illustrates the fluid flow path defined by the centrifugal separation chamber 32. In the illustrated embodiment, the body of the centrifugal separation chamber 32 is pre-formed in a desired shape and configuration (e.g., by injection molding) from a rigid, biocompatible plastic material, such as a non-plasticized medical grade acrylonitrile-butadiene-styrene (ABS). All contours, ports, channels, and walls that affect the fluid separation process are preformed in a single, injection molded operation. Alternatively, the centrifugal separation chamber 32 can be formed by separate molded parts, either by nesting cup-shaped subassemblies or two symmetric halves.

The underside of the centrifugal separation chamber 32 includes a shaped receptacle 56 that is suitable for receiving an end of the umbilicus 46 of the fluid flow circuit 12 (FIG. 3). A suitable receptacle 56 and the manner in which the umbilicus 46 may cooperate with the receptacle 56 to deliver fluid to and remove fluid from the centrifugal separation chamber 32 are described in greater detail in U.S. Pat. No. 8,075,468.

The illustrated centrifugal separation chamber 32 has radially spaced apart inner (low-g) and outer (high-g) side wall portions 58 and 60, a bottom or first end wall portion 62, and a cover or second end wall portion 64. The cover 64 comprises a simple flat part that can be easily welded or otherwise secured to the body of the centrifugal separation chamber 32. The wall portions 58 and 60, the bottom 62, and the cover 64 together define an enclosed, generally annular channel 66 (FIG. 10).

An inlet 68 communicating with the channel 66 is defined between opposing interior radial walls 70 and 72. One of the interior walls 70 joins the outer (high-g) wall portion 60 and separates the upstream and downstream ends of the channel 66. The interior walls 70 and 72 define the inlet passageway 68 of the centrifugal separation chamber 32 which, in one flow configuration, allows fluid to flow from the umbilicus 46 to the upstream end of the channel 66.

The illustrated centrifugal separation chamber 32 further includes first and second outlets 74 and 76, respectively, which may be defined by opposing surfaces of interior radial walls. Both the first and second outlets 74 and 76 extend radially inward from the channel 66. The first outlet 74 extends radially inward from an opening which, in the illustrated embodiment, is located at the inner side wall portion 58, while the second outlet 76 extends radially inward from an opening that is associated with the outer side wall portion 60. The illustrated first outlet 74 is positioned adjacent to the inlet 68 (near the upstream end of the channel 66), while the second outlet 76 may be positioned at the opposite, downstream end of the channel 66.

It should be understood that the centrifugal separation chamber 32 illustrated in FIG. 8 is merely exemplary and that the centrifugal separation chamber 32 may be differently configured without departing from the scope of the present disclosure. For example, PCT Patent Application Publication No. WO 2018/053217 A1 describes other exemplary centrifugal separation chamber configurations. Additionally, as noted above, while the principles regarding adjustment of a component of a detection assembly are described herein in the context of a detection assembly that monitors fluid separation within the centrifugal separation chamber 32, it should be understood that such principles are applicable to detection assemblies configured to monitor other subjects.

1. Centrifugal Separation and Interface Detection Principles

Fluid flowed into the channel 66 separates into an optically dense layer "R" and a less optically dense layer "P"

(FIGS. 11-13) as the centrifugal separation chamber 32 is rotated about the rotational axis 38. The optically dense layer R forms as larger and/or heavier fluid particles move under the influence of centrifugal force toward the outer (high-g) wall portion 60. If the fluid being separated is blood, the optically dense layer R will typically include red blood cells but, depending on the speed at which the centrifugal separation chamber 32 is rotated, other cellular components (e.g., larger white blood cells) may also be present in the optically dense layer R.

If the fluid being separated is blood, the less optically dense layer P typically includes a plasma constituent, such as platelet-rich plasma or platelet-poor plasma. Depending on the speed at which the centrifugal separation chamber 32 is rotated and the length of time that the blood is resident therein, other components (e.g., smaller white blood cells and anticoagulant) may also be present in the less optically dense layer P.

In one embodiment, fluid introduced into the channel 66 via the inlet 68 will travel in a generally clockwise direction (in the orientation of FIG. 8) as the optically dense layer R separates from the less optically dense layer P. The optically dense layer R continues moving in the clockwise direction as it travels the length of the channel 66 along the outer side wall portion 60, from the upstream end to the downstream end, where it exits the channel 66 via the second outlet 76. The less optically dense layer P separated from the optically dense layer R reverses direction, moving counterclockwise along the inner side wall portion 58 to the first outlet 74, adjacent to the inlet 68.

Figure 11:
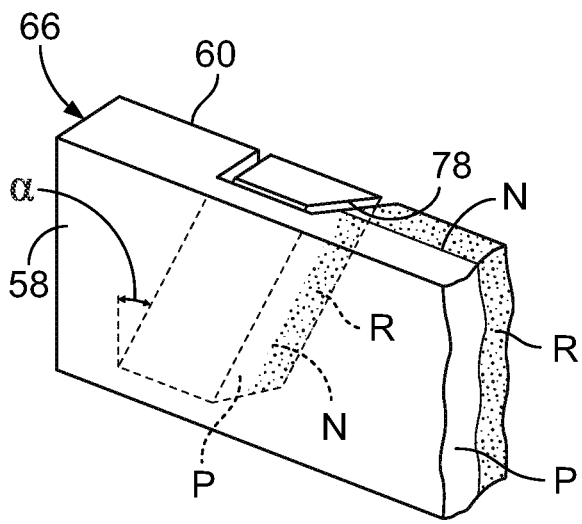
FIG. 11 is an enlarged perspective view of a portion of a channel of the centrifugal separation chamber of FIGS. 8-10, with an interface between separated fluid components being positioned at a (typically) desired location on a ramp defined within the channel.
Figure 12:
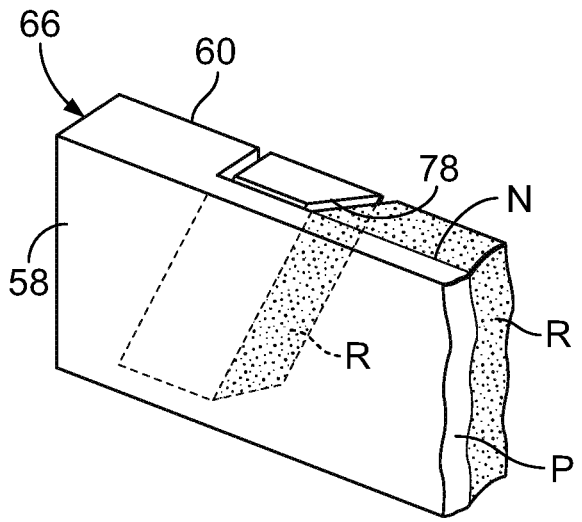
FIG. 12 is an enlarged perspective view of the channel and ramp of FIG. 11, with the interface being at a (typically) undesired high location on the ramp.
Figure 13:
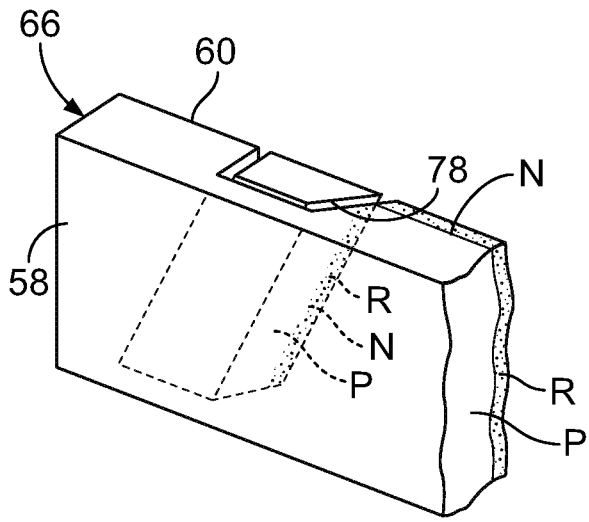
FIG. 13 is an enlarged perspective view of the channel and ramp of FIG. 11, with the interface being at a (typically) undesired low location on the ramp.

The transition between the optically dense layer R and the less optically dense layer P may be referred to as the interface "N". If the fluid being separated is blood, the interface N contains mononuclear cells and peripheral blood stem cells. The location of the interface N within the channel 66 of the centrifugal separation chamber 32 can dynamically shift during fluid processing, as FIGS. 11-13 show. If the location of the interface N is too high (that is, if it is too close to the inner side wall portion 58 and the first outlet 74, as in FIG. 12), red blood cells can flow into the first outlet 74, potentially adversely affecting the quality of the low density components (platelet-rich plasma or platelet-poor plasma). On the other hand, if the location of the interface N is too low (that is, if it resides too far away from the inner wall portion 58, as FIG. 13 shows), the collection efficiency of the system may be impaired. The ideal or target interface location may be experimentally determined, which may vary depending on any of a number of factors (e.g., the configuration of the centrifugal separation chamber 32, the rate at which the centrifugal separation chamber 32 is rotated about the rotational axis 38, etc.).

As described above, the fluid processing device 10 may include interface monitoring assembly (including the light source 50 and the light detector 52), a centrifuge outlet sensor D1, and a controller 18 with an interface control module to monitor and, as necessary, adjust or correct the position of the interface N In the illustrated embodiment, the centrifugal separation chamber 32 is formed with a ramp 78 extending from the high-g wall portion 60 at an angle α across at least a portion of the channel 66 (FIGS. 8 and 11-13). The angle α, measured with respect to the rotational axis 38 is about 25° in one embodiment. FIGS. 11-13 show the orientation of the ramp 78 when viewed from the low-g side wall portion 58 of the centrifugal separation chamber 32. Although it describes a flexible separation chamber, the general structure and function of the ramp 78 may be better understood with reference to U.S. Pat. No. 5,632,893, which is hereby incorporated herein by reference.

The ramp 78 makes the interface N between the optically dense layer R and the less optically dense layer P more discernible for detection, displaying the optically dense layer R, less optically dense layer P, and interface N for viewing through a light-transmissive portion of the centrifugal separation chamber 32. To that end, the ramp 78 and at least the portion of the centrifugal separation chamber 32 angularly aligned with the ramp 78 may be formed of a light-transmissive material, although it may be advantageous for the entire centrifugal separation chamber 32 to be formed of the same light-transmissive material.

In the illustrated embodiment, the light source 50 of the interface monitoring system is associated with a fixture or wall of the centrifuge compartment 34 and oriented to emit a light L that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 58, as shown in FIGS. 5 and 6. The reflector may be a separate piece that is secured to the inner side wall portion 58 (e.g., by being bonded thereto) or may be integrally formed with the body of the centrifugal separation chamber 66.

Figure 14:
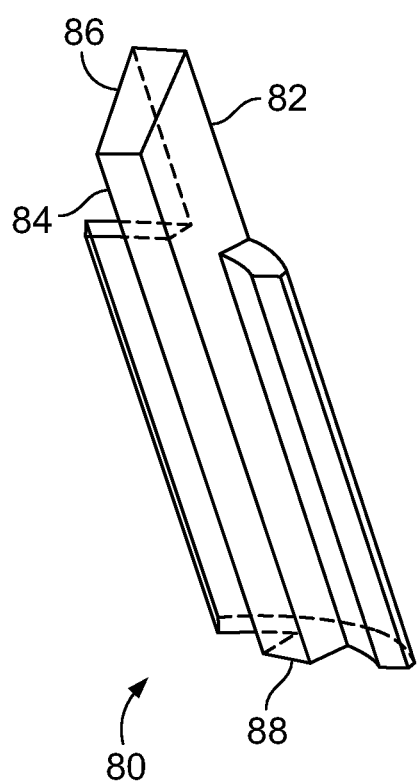
FIG. 14 is a perspective view of a prismatic reflector used in combination with the centrifugal separation chamber of FIGS. 8-10.

In one embodiment, the reflector may be a reflective surface, such as a mirror, that is oriented (e.g., at a 450 angle) to direct light L emitted by the light source 50 to the light detector 52. In another embodiment, the reflector is provided as a prismatic reflector 80 (FIGS. 7, 14, and 15), which is formed of a light-transmissive material (e.g., a clear plastic material) and has inner and outer walls 82 and 84 and first and second end walls 86 and 88 (FIG. 14). The inner wall 82 is positioned against the inner side wall portion 58 of the centrifugal separation chamber 32 and is oriented substantially perpendicular to the initial path of the light L from the light source 50. This allows light L from the light source 50 to enter into the prismatic reflector 80 via the inner wall 82 while continuing along its initial path. The light L continues through the prismatic reflector 80 along its initial path until it encounters the first end wall 86. The first end wall 86 is oriented at an angle (e.g., an approximately 45° angle) with respect to the inner wall 82 and the second end wall 88, causing the light L to be redirected within the prismatic reflector 80, rather than exiting the prismatic reflector 80 via the first end wall 86.

Figure 15:
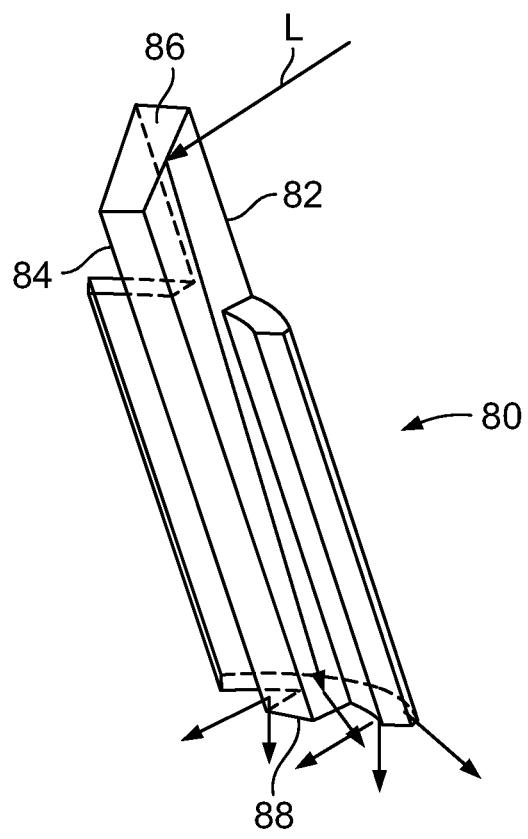
FIG. 15 is a perspective view of the prismatic reflector of FIG. 14, showing light being transmitted therethrough.

The first end wall 86 directs the light L at an angle to its initial path (which may be an approximately 90° angle, directing it from a path toward the rotational axis 38 to a path that is generally parallel to the rotational axis 38) toward the second end wall 88 (FIG. 15). The first end wall 86 and the inner and outer walls 82 and 84 of the prismatic reflector 80 may be configured to transmit the redirected light L from the first end wall 86 to the second end wall 88 by total internal reflection. The second end wall 88 is oriented substantially perpendicular to the redirected path of the light L through the prismatic reflector 80, such that the light L will exit the prismatic reflector 80 via the second end wall 88, continuing along its redirected path. In one embodiment, the second end wall 88 is roughened or textured or otherwise treated or conditioned to diffuse the light L as it exits the prismatic reflector 80, which may better ensure that the light L reaches the light detector 52 (FIG. 7).

The prismatic reflector 80 may be angularly aligned with the ramp 78, such that the light L from the light source 50 will only enter into the prismatic reflector 80 when the ramp 78 has been rotated into the path of the light L. At all other times (when the ramp 78 is not in the path of the light L), the light L will not reach the prismatic reflector 80 and, thus, will not reach the light detector 52.

Upon the ramp 78 first being rotated into the path of the light L from the light source 50, the light L will begin to reach the prismatic reflector 80, which directs the light L to the light detector 52. This causes the voltage output of the light detector 52 (i.e., the signal transmitted from the light detector 52 to the controller 18) to increase to a non-zero value or state. The ramp 78 and prismatic reflector 80 are eventually rotated out of alignment with the light source 50, at which time no light L will reach the prismatic reflector 80 and the voltage output of the light detector 52 will return to a low- or zero-state.

During the time that the ramp 78 and prismatic reflector 80 are rotated through the path of the light L from the light source 50, the light L continues through the channel 66 and the fluids in the channel 66. At least a portion of the light L (i.e., the portion not absorbed or reflected by the fluids) exits the channel 66 by striking and entering a light-transmissive portion of the inner side wall portion 58. The light L passes through the inner side wall portion 58 and enters the prismatic reflector 80, which redirects the light L from its initial path to the light detector 52, as described above.

The light detector 52 generates a signal that is transmitted to the interface control module of the controller 18, which can determine the location of the interface N on the ramp 78. In one embodiment, the location of the interface N is associated with a change in the amount of light L that is transmitted through the less optically dense layer P and the optically dense layer R. For example, the light source 50 may be configured to emit a light L that is more readily transmitted by platelet-rich plasma or platelet-poor plasma than by red blood cells, such as red visible light (from a laser or a differently configured light source L), which is substantially absorbed by red blood cells. The less optically dense layer P and the optically dense layer R each occupy a certain portion of the ramp 78, with the light detector 52 receiving different amounts of light L depending on whether the light L travels through the less optically dense layer P on the ramp 78 or the optically dense layer R on the ramp 78. The percentage of the ramp 78 occupied by each layer is related to the location of the interface N in the channel 66. Thus, by measuring the amount of time that the voltage output or signal from the light detector 52 is relatively high (corresponding to the time during which the light L is passing through only the less optically dense layer P on the ramp 78), the controller 18 may determine the location of the interface N and take steps to correct the location of the interface N, if necessary. An exemplary approach to adjustment of the position of the interface N is described in greater detail in PCT Patent Application Publication No. WO 2018/053217 A1.

2. Adjustment of Component(s) of Detection Assembly

It will be appreciated that light L from the light source 50 must reach the light detector 52 to determine (and adjust) the location of the interface N. The initial or default orientation and position of the light source 50 and the light detector 52 assumes a particular orientation and position of the prismatic reflector 80, which depends upon the proper installation and orientation of the centrifugal separation chamber 32 into the centrifuge compartment 34. Thus, if the centrifugal separation chamber 32 is not properly installed and oriented, the prismatic reflector 80 may not be capable of properly directing light L from the light source 50 to the light detector 52. Even if the centrifugal separation chamber 32 is properly installed and oriented, it may be the case that the prismatic reflector 80 is not ideally positioned and/or oriented to direct light L from the light source 50 to the light detector 52 (e.g., due to an imperfection in the configuration of the centrifugal separation chamber 32).

According to an aspect of the present disclosure, the interface monitoring assembly includes an adjustment system 90 (FIG. 16) associated with the light source 50 and configured to adjust the position and/or orientation of the light source 50 with respect to the portion of the centrifuge compartment 34 with which the light source 50 is associated. The adjustment system 90 may be variously configured without departing from the scope of the present disclosure, but in the illustrated embodiment comprises three elongated legs 92 secured to a wall or surface of the centrifuge compartment 34. The three legs 92 are arranged in an equilateral triangle and are substantially parallel to each other, extending orthogonally from the wall of the centrifuge compartment 34. An aperture or opening 94 is defined in the wall of the centrifuge compartment 34 in the space between the legs 92, which allows light L from the light source 50 to pass through the wall of the centrifuge compartment 34 to reach a centrifugal separation chamber 34 mounted within the centrifuge compartment 34.

Each leg 92 includes an associated support 96, which is movable along at least a portion of the length of the leg 92, toward and away from the wall of the centrifuge compartment 34. The supports 96 may be movable by any suitable drive mechanism, such as a motor, with the supports 96 being movable independently of each other.

Each support 96 includes an arm 98 extending between the support 96 and the light source 50. The ends of each arm 98 are pivotally connected to the light source 50 and the associated support 96 to allow for adjustment of the position of the light source 50 with respect to the support 96. This arrangement allows the light source 50 to be moved into a wide range of positions within the three-dimensional space defined between the legs 92, with each support 96 being movable along the respective leg 92 to the necessary position to accommodate the position desired for the light source 50. In addition to allowing adjustment of the position of the light source 50 with respect to the associated wall of the centrifuge compartment 34, the illustrated arrangement also allows for the orientation of the light source 50 with respect to the wall of the centrifuge compartment 34 to be adjusted, such that the light source 50 may be arranged to emit light L through the aperture or opening 94 at a variety of angles.

In addition to (or instead of) any adjustment system associated with the light source 50, an adjustment system may be associated with the light detector 52 and configured to adjust the position and/or orientation of the light detector 52 with respect to the portion of the centrifuge compartment 34 with which the light detector 52 is associated. The adjustment system associated with the light detector 52 may be variously configured without departing from the scope of the present disclosure, but in the illustrated embodiment of FIG. 17, the adjustment system 100 comprises a frame 102 connected to a wall or surface of the centrifuge compartment 34. The frame 102 includes two substantially parallel legs 104 extending orthogonally from the wall of the centrifuge compartment 34, with a crossbar 106 extending between the legs 104. An aperture or opening 108 is defined in the wall of the centrifuge compartment 34 in the space between the legs 104, which allows light L to pass through the wall of the centrifuge compartment 34 to reach the light detector 52.

The upper end of each leg 104 (in the orientation of FIG. 17) is associated with a track, allowing the frame 102 to be moved in a direction transverse to the length of the crossbar 106. The frame 102 may be moved along the track by any suitable drive mechanism, such as a motor. This direction of movement may be understood as movement in the "x" direction of a Cartesian coordinate system.

The light detector 52 is associated to the crossbar 106 by a support 110, which is movable along at least a portion of the length of the crossbar 106, toward and away from the legs 104 at each end of the crossbar 106. The support 110 may be movable by any suitable drive mechanism, such as a motor. This direction of movement may be understood as movement in the "y" direction of a Cartesian coordinate system.

In one embodiment, the crossbar 106 is configured for movement along at least a portion of the lengths of the legs 104, toward and away from the wall of the centrifuge compartment 34. In another embodiment, the crossbar 106 may be fixedly secured to the legs 104, while the support 110 (or a portion thereof) is movable with respect to the crossbar 106 in a direction that is parallel to the lengths of the legs 104, toward and away from the wall of the centrifuge compartment 34. In either case, such movement may be implemented by any suitable drive mechanism, such as a motor. This direction of movement may be understood as movement in the "z" direction of a Cartesian coordinate system.

The illustrated arrangement thus allows the light detector 52 to be moved into a wide range of positions within the three-dimensional space above the aperture or opening 108 defined in the wall of the centrifuge compartment 34. In addition to allowing adjustment of the position of the light detector 52 with respect to the associated wall of the centrifuge compartment 34, the illustrated arrangement may also allow for the orientation of the light detector 52 with respect to the wall of the centrifuge compartment 34 to be adjusted. This may be achieved, for example, by allowing the support 110 or a portion thereof to pivot with respect to the crossbar 106, thereby allowing the light detector 52 to be arranged to receive light L through the aperture or opening 108 at a variety of angles.

Figure 16:
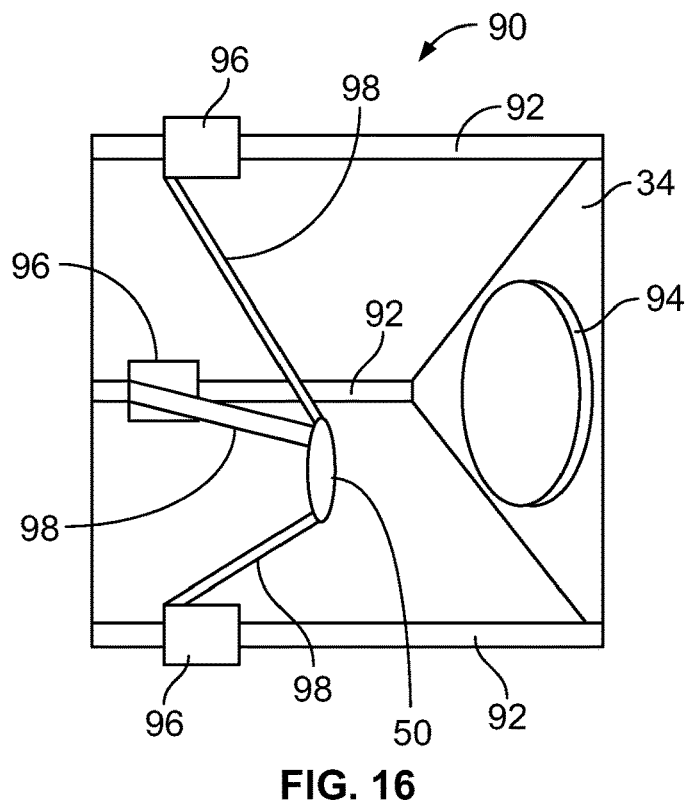
FIG. 16 is a schematic view of an exemplary mechanism for adjusting the position and/or orientation of a component of a detection assembly.
Figure 17:
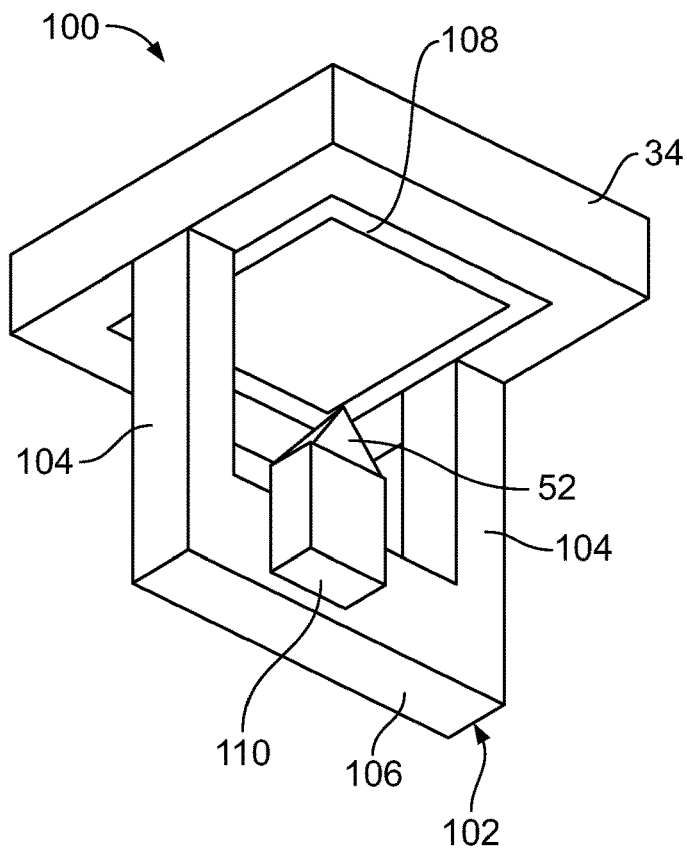
FIG. 17 is a schematic view of another exemplary mechanism for adjusting the position and/or orientation of a component of a detection assembly.

It should be understood that the adjustment systems 90 and 100 of FIGS. 16 and 17 are merely exemplary and that adjustment systems for adjusting the position and/or orientation of the source and detector of a detection assembly may be differently configured without departing from the scope of the present disclosure. For example, an adjustment system of the type shown in FIG. 17 may be employed in combination with a source, while an adjustment system of the type shown in FIG. 16 may be employed in combination with a detector. In other embodiments, an adjustment system may be configured to only adjust the position of a source or a detector (without adjusting the orientation of the source or detector) or to adjust only the orientation of a source or a detector (without adjusting the position of the source or detector). Further, adjusting the orientation of a source or a detector is not limited to adjusting the angle or tilt of the source or detector, but may also include rotating the source or detector about its central axis. It should also be understood that the adjustment of the source or detector of a detection assembly is not limited to detection assemblies using light, but may be used in combination with detection assemblies transmitting other signals from the source to the detector (e.g., an ultrasonic detection assembly).

The adjustment system associated with a detection assembly may be controlled by the controller 18 of the fluid processing device 10. The source and detector of a detection assembly may be provided in initial positions and orientations. When the controller 18 determines that it would be desirable to reposition and/or reorient the source and/or the detector, the controller 18 may issue commands to the appropriate drive mechanisms of the associated adjustment system(s) to move the source and/or the detector to a new position and/or into a new orientation. The controller 18 may determine that repositioning and/or reorientation of a component of a detection assembly is desirable according to any suitable approach. In one embodiment, the controller 18 may receive a signal from the detector, which is compared to an expected signal. In the case of an interface monitoring assembly, saline may be conveyed through a fluid flow circuit 12 mounted to the fluid processing device 10 to prime the fluid flow circuit 12. The light L transmitted to the light detector 52 will have certain characteristics, which results in a particular signal being sent from the light detector 52 to the controller 18. If the nature of the light L received by the light detector 52 is different from the nature of the light L expected to be received by the light detector 52 after the light L has passed through saline, there will be a difference between one or more corresponding characteristic(s) of the signal that is actually transmitted to the controller 18 from the light detector 52 and the expected signal (e.g., the voltage of the signal). If one or more characteristics of the signal differ from the corresponding characteristic(s) of the expected signal, the controller 18 may determine that the performance of the detection assembly may be improved by adjusting the position and/or orientation of the source and/or the detector.

Alternatively, rather than comparing the signal from the detector to an expected signal, the controller 18 may instead be configured to issue commands to the appropriate drive mechanisms of the associated adjustment system(s) to move the source and/or the detector into a variety of new positions and/or orientations. During this repositioning and/or reorientation, the source continues transmitting a signal that is at least partially received by the detector, with the detector transmitting a signal to the controller 18 that is indicative of the nature of the signal received by the detector. The controller 18 monitors the signal being transmitted to it from the detector to determine when the signal has optimal properties (e.g., when the signal has a maximum voltage) and then commands the adjustment system(s) to move the source and/or the detector into the position and/or orientation resulting in the optimal signal. It may be advantageous for such an adjustment procedure to take place before fluid processing has begun in order to avoid introducing any factors (other than the adjustment being made to the component(s) of the detection assembly) that would tend to change the nature of the signals received and transmitted by the detector. However, it is within the scope of the present disclosure for such an adjustment procedure to occur during fluid processing, particularly when a steady state has been reached.

Frequently, the need for adjustment of the position and/or orientation of a component of a detection assembly arises due to the alignment of a component of a fluid flow circuit 12 mounted to the fluid processing device 10. Thus, in another embodiment, a detection assembly may be configured to transmit an orientation signal to the controller 18, which signal may be indicative of the position and/or orientation of a component of the fluid flow circuit 12. If the orientation signal indicates to the controller 18 that performance of the detection assembly would be improved by adjustment of the position and/or orientation of any of the components of the detection assembly, the controller 18 may command the appropriate adjustment systems to properly position and/or orient such component(s). In one embodiment, a component of a fluid flow circuit may be provided with one or more markers that are indicative of the orientation of the component when mounted to a fluid processing device. The detection assembly determines the location of the marker(s) and transmits that information to the controller of the fluid processing device as an orientation signal. If the controller determines that one or more of the markers is not properly positioned (e.g., by comparing the orientation signal to an expected signal), the controller commands the appropriate adjustment systems to properly position and/or orient the components of the detection assembly. For example, if the markers are oriented in a square around a target location of the component for receiving a signal from the source, the controller may cause the source to be repositioned and/or reoriented to align the source with the target location at the center of the square defined by the markers. Other indicia besides markers (e.g., a region of a component of the fluid flow circuit having a particular thickness, which uniquely affects the amount of light received by the detector) and other approaches may be employed to determine the position and orientation of a component of the fluid flow circuit.

Even when a monitored component of a fluid flow circuit 12 has been properly installed, it may be appropriate to adjust the position and/or orientation of one or more components of a detection assembly. For example, if a fluid processing device is configured to execute a variety of procedures, the fluid flow circuits unique to each procedure may be differently configured in a way that requires adjustment of the position and/or orientation of at least one component of a detection assembly. In the illustrated embodiment, this may include differently configured centrifugal separation chambers with differently configured prismatic reflectors, with at least two of the centrifugal separation chambers being optimally monitored by the same detection assembly having differently positioned and/or oriented components.

As the alignment and configuration of a component of a fluid flow circuit 12 will not tend to change during a procedure, it may be sufficient for adjustment of a detection assembly to be carried out once, such as during a calibration stage of a procedure. For example, adjustment may be made to one or more detection assemblies once a fluid flow circuit 12 has been mounted to the fluid processing device 10, before the fluid flow circuit 12 is primed. In another embodiment, adjustments are made during some other early phase of the procedure, such as while the fluid flow circuit 12 is being primed. Once the necessary adjustments have been made, the positions and orientations of the detection assemblies may be fixed with respect to the associated structure or component of the fluid processing device for the rest of a procedure. However, while it will typically be sufficient to make adjustments only once, it is also but may also within the scope of the present disclosure for adjustments to be made to the components of a detection assembly more than once during a procedure, as may be necessary if the position and/or orientation of a component of a fluid flow circuit changes unexpectedly during a procedure.

Rather than (or in addition to) adjusting the position and/or orientation of an entire source or detector, an adjustment system may be configured to adjust the position and/or orientation of a component of the source or detector with respect to another component of the same device. For example, in the case of a source configured to emit a light, a lens of the source may be repositioned and/or reoriented with respect to another component of the source to change its focal point. Other dynamic adjustments to individual components of a source or a detector may also be controlled by the controller 18, with the particular configuration of the associated adjustment system depending upon the nature of adjustments to be made to a component. It should be understood that the above-described approaches to the controller 18 determining the need for an adjustment to a source or a detector and then implementing such an adjustment are equally applicable to adjustment of individual components of a source or detector. Thus, the position and/or orientation of an entire source or detector may be adjusted during a procedure (e.g., during a calibration stage and/or during a fluid separation stage), while adjustments may also be made to individual components of the source or detector at the same time(s).

While the detection assemblies of the illustrated fluid processing device 10 are associated with stationary components or structures of the fluid processing device 10, the adjustment principles described herein may be employed in combination with detection assemblies having components associated with movable components of a fluid processing device. Thus, it should be understood that adjustment of the position and/or orientation of a component of a detection assembly by action of an adjustment system according to the present disclosure is different from the change in position and orientation that occurs when such a component is incorporated into a movable component or structure of a fluid processing device, but instead occurs when the position and/or orientation of such a component of the detection assembly is adjusted with respect to the component or structure of the fluid processing device with which the component of the detection assembly is associated. For example, if the light source 50 of the interface monitoring assembly were incorporated into the yoke member 44, movement of the entire yoke member 44 during a fluid separation procedure would not be considered as an adjustment of the position and/or orientation of the light source 50 implemented by an adjustment system according to the present disclosure. Instead, an adjustment system would be configured to reposition and/or reorient the light source 50 with respect to the yoke member 44 itself.

According to yet another aspect of the present disclosure, the nature of the signal emitted by the source 50 may be adjusted. For example, when the source 50 is provided as a light source configured to emit light having a single wavelength (or light having a plurality of wavelengths in a particular range), the adjustment system may be configured to adjust the light source 50 to emit light having a different wavelength (or light having a plurality of wavelengths in a different range). This may be achieved, for example, by providing a plurality of light sources (e.g., a plurality of lasers configured to emit differently colored lights), with only one being active at a time. When it is determined that a different type of light would be advantageous (e.g., based on a different fluid property being assessed or feedback from the controller 18 indicating that a different light may improve performance of the detection assembly), the controller 18 may instruct the adjustment system to deactivate one light source and activate another. This may include exchanging the positions of two light sources or moving a first light source out of position and moving a second light source into the position formerly occupied by the first light source. In such a configuration, any number of light sources may be provided. It should be understood that this is only one possible approach to adjusting the nature of the signal emitted by the source 50 and that other approaches may be employed without departing from the scope of the present disclosure. It should also be understood that, depending on the particular mechanism employed to adjust the nature of the signal, such an adjustment may be considered to be an adjustment of the position and/or orientation of the source 50.

Similarly, just as the nature of the signal emitted by the source 50 may be adjusted, the nature of the detector 52 may be adjusted by an adjustment system according to the present disclosure. For example, when the detector 50 is provided as a light detector configured to analyze light having a single wavelength (or light having a plurality of wavelengths in a particular range), the adjustment system may be configured to adjust the light detector 50 to analyze light having a different wavelength (or light having a plurality of wavelengths in a different range). This may be achieved, for example, by providing a plurality of filters, which are each configured to filter out different wavelengths of light. When it is determined that analyzing a different wavelength or range of wavelengths of light would be advantageous (e.g., based on a different fluid property being assessed or feedback from the controller 18 indicating that analyzing a different wavelength or range of wavelengths may improve performance of the detection assembly), the controller 18 may instruct the adjustment system to replace one filter with another (or to employ a filter, if one is not currently being used). This may include exchanging the positions of two filters or moving a first filter out of position and moving a second filter into the position formerly occupied by the first filter. Any number of filters may be employed, such that this adjustment may also include the controller 18 instructing the adjustment system to activate two or more filters simultaneously or instructing the adjustment system to deactivate all of the filters. It should be understood that this is only one possible approach to adjusting the nature of the detector 52 and that other approaches may be employed without departing from the scope of the present disclosure. It should also be understood that, depending on the particular mechanism employed to adjust the nature of the detector 52, such an adjustment may be considered to be an adjustment of the position and/or orientation of the detector 52.

Aspects

Aspect 1. A fluid processing device, comprising: a detection assembly including a source associated with a component of the fluid processing device, provided in an initial position and an initial orientation with respect to said component of the fluid processing device, and configured to emit a signal, and a detector associated with a structure of the fluid processing device, provided in an initial position and an initial orientation with respect to said structure of the fluid processing device, and configured to receive at least a portion of the signal; and a controller, wherein the detection assembly further includes an adjustment system associated with the source, with the controller being configured to control the adjustment system to adjust the position and/or the orientation of the source with respect to said component of the fluid processing device and/or a position and/or an orientation of a component of the source with respect to another component of the source, and/or an adjustment system associated with the detector, with the controller being configured to control the adjustment system to adjust the position and/or the orientation of the detector with respect to said structure of the fluid processing device and/or a position and/or an orientation of a component of the detector with respect to another component of the detector.

Aspect 2. The fluid processing device of Aspect 1, wherein the source is associated with a stationary component of the fluid processing device.

Aspect 3. The fluid processing device of Aspect 1, wherein the source is associated with a movable component of the fluid processing device.

Aspect 4. The fluid processing device of any one of the preceding Aspects, wherein the detector is associated with a stationary structure of the fluid processing device.

Aspect 5. The fluid processing device of any one of Aspects 1-3, wherein the detector is associated with a movable structure of the fluid processing device.

Aspect 6. The fluid processing device of any one of the preceding Aspects, wherein the controller is configured to receive a signal from the detector, compare the signal from the detector to an expected signal from the detector, and when the signal from the detector has a characteristic that is less than a corresponding characteristic of the expected signal, control the adjustment system associated with the source to adjust the position and/or the orientation of the source with respect to said component of the fluid processing device and/or the position and/or the orientation of said component of the source with respect to said another component of the source and/or to control the adjustment system associated with the detector to adjust the position and/or the orientation of the detector with respect to said structure of the fluid processing device and/or the position and/or the orientation of said component of the detector with respect to said another component of the detector to increase said characteristic of the signal from the detector.

Aspect 7. The fluid processing device of any one of the preceding Aspects, wherein the fluid processing device is configured to accommodate a fluid flow circuit for conducting fluid flow through the fluid processing device, and the controller is configured to receive an orientation signal indicative of a position and/or an orientation of a component of a fluid flow circuit associated to the fluid processing device, determine whether the position and/or the orientation of said component of the fluid flow circuit is different from an expected position and/or an expected orientation, and when the position and/or the orientation of said component of the fluid flow circuit is different from the expected position and/or the expected orientation, control the adjustment system associated with the source to adjust the position and/or the orientation of the source with respect to said component of the fluid processing device and/or the position and/or the orientation of said component of the source with respect to said another component of the source and/or to control the adjustment system associated with the detector to adjust the position and/or the orientation of the detector with respect to said structure of the fluid processing device and/or the position and/or the orientation of said component of the detector with respect to said another component of the detector to account for the position and/or the orientation of said component of the fluid flow circuit.

Aspect 8. The fluid processing device of any one of the preceding Aspects, wherein the adjustment system associated with the source is configured to adjust the position of the source and/or of the component of the source in three dimensions.

Aspect 9. The fluid processing device of any one of the preceding Aspects, wherein the adjustment system associated with the detector is configured to adjust the position of the detector and/or of the component of the detector in three dimensions.

Aspect 10. The fluid processing device of any one of the preceding Aspects, wherein the source comprises a light source and the detector comprises a light detector.

Aspect 11. The fluid processing device of Aspect 10, wherein said component of the source comprises a lens.

Aspect 12. A method of monitoring a fluid and/or a fluid component in a fluid processing device including a source and a detector, the source being associated with a component of the fluid processing device and provided in an initial position and an initial orientation with respect to said component of the fluid processing device, and the detector being associated with a structure of the fluid processing device and provided in an initial position and an initial orientation with respect to said structure of the fluid processing device, the method comprising: emitting a signal from the source and to a fluid and/or a fluid component in the fluid processing device; receiving at least a portion of the signal with the detector; and adjusting the position and/or the orientation of the source with respect to said component of the fluid processing device, the position and/or the orientation of the detector with respect to said structure of the fluid processing device, a position and/or an orientation of a component of the source with respect to another component of the source, and/or a position and/or an orientation of a component of the detector with respect to another component of the detector.

Aspect 13. The method of Aspect 12, wherein the source is stationary while emitting said signal.

Aspect 14. The method of Aspect 12, wherein the source is moving while emitting said signal.

Aspect 15. The method of any one of Aspects 12-14, wherein the detector is stationary while receiving said at least a portion of the signal.

Aspect 16. The method of any one of Aspects 12-14, wherein the detector is moving while receiving said at least a portion of the signal.

Aspect 17. The method of any one of Aspects 12-16, further comprising comparing a signal from the detector to an expected signal from the detector, and when the signal from the detector has a characteristic that is less than a corresponding characteristic of the expected signal, adjusting the position and/or the orientation of the source with respect to said component of the fluid processing device and/or the position and/or the orientation of said component of the source with respect to said another component of the source and/or adjusting the position and/or the orientation of the detector with respect to said structure of the fluid processing device and/or the position and/or the orientation of said component of the detector with respect to said another component of the detector to increase said characteristic of the signal from the detector.

Aspect 18. The method of any one of Aspects 12-17, wherein the fluid processing device is configured to accommodate a fluid flow circuit for conducting fluid flow through the fluid processing device, and further comprising determining whether a position and/or an orientation of a component of a fluid flow circuit accommodated by the fluid processing device is different from an expected position and/or an expected orientation, and when the position and/or the orientation of said component of the fluid flow circuit is different from the expected position and/or the expected orientation, adjusting the position and/or the orientation of the source with respect to said component of the fluid processing device and/or the position and/or the orientation of said component of the source with respect to said another component of the source and/or adjusting the position and/or the orientation of the detector with respect to said structure of the fluid processing device and/or the position and/or the orientation of said component of the detector with respect to said another component of the detector to account for the position and/or the orientation of said component of the fluid flow circuit.

Aspect 19. The method of any one of Aspects 12-18, wherein the source comprises a light source and the detector comprises a light detector.

Aspect 20. The method of Aspect 19, wherein said component of the source comprises a lens.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing device, comprising:
a detection assembly including
a source associated with a component of the fluid processing device, provided in an initial position and an initial orientation with respect to said component of the fluid processing device, and configured to emit a signal, and
a detector associated with a structure of the fluid processing device, provided in an initial position and an initial orientation with respect to said structure of the fluid processing device, and configured to receive at least a portion of the signal; and
a controller, wherein
the detection assembly further includes
an adjustment system associated with the source, with the controller being configured to control the adjustment system to execute a source adjustment in which the position and/or the orientation of the source is adjusted with respect to said component of the fluid processing device and/or a position and/or an orientation of a component of the source is adjusted with respect to another component of the source, and/or
an adjustment system associated with the detector, with the controller being configured to control the adjustment system to execute a detector adjustment in which the position and/or the orientation of the detector is adjusted with respect to said structure of the fluid processing device and/or a position and/or an orientation of a component of the detector is adjusted with respect to another component of the detector, and
the controller is configured to
control the adjustment system associated with the source to execute a plurality of different source adjustments when the detection assembly includes the adjustment system associated with the source and/or control the adjustment system associated with the detector to execute a plurality of different detector adjustments when the detection assembly includes the adjustment system associated with the detector, receive signals from the detector for each of said plurality of different source adjustments and/or detector adjustments, compare the signals from the detector to each other to determine the source adjustment and/or detector adjustment in which the signal from the detector has maximum voltage, and control the adjustment system associated with the source to execute the source adjustment in which the signal from the detector has maximum voltage when the detection assembly includes the adjustment system associated with the source and/or control the adjustment system associated with the detector to execute the detector adjustment in which the signal from the detector has maximum voltage when the detection assembly includes the adjustment system associated with the detector.

2. The fluid processing device of claim 1, wherein the source is associated with a stationary component of the fluid processing device.

3. The fluid processing device of claim 1, wherein the source is associated with a movable component of the fluid processing device.

4. The fluid processing device of claim 1, wherein the detector is associated with a stationary structure of the fluid processing device.

5. The fluid processing device of claim 1, wherein the detector is associated with a movable structure of the fluid processing device.

6. The fluid processing device of claim 1, wherein the adjustment system associated with the source is configured to adjust the position of the source and/or of the component of the source in three dimensions.

7. The fluid processing device of claim 1, wherein the adjustment system associated with the detector is configured to adjust the position of the detector and/or of the component of the detector in three dimensions.

8. The fluid processing device of claim 1, wherein the source comprises a light source and the detector comprises a light detector.

9. The fluid processing device of claim 8, wherein said component of the source comprises a lens.

10. A fluid processing device, comprising:
a detection assembly including
a source associated with a component of the fluid processing device, provided in an initial position and an initial orientation with respect to said component of the fluid processing device, and configured to emit a signal, and
a detector associated with a structure of the fluid processing device, provided in an initial position and an initial orientation with respect to said structure of the fluid processing device, and configured to receive at least a portion of the signal; and
a controller, wherein
the detection assembly further includes
an adjustment system associated with the source, with the controller being configured to control the adjustment system to execute a source adjustment in which the position and/or the orientation of the source is adjusted with respect to said component of the fluid processing device and/or a position and/or an orientation of a component of the source is adjusted with respect to another component of the source, and/or
an adjustment system associated with the detector, with the controller being configured to control the adjustment system to execute a detector adjustment in which the position and/or the orientation of the detector is adjusted with respect to said structure of the fluid processing device and/or a position and/or an orientation of a component of the detector is adjusted with respect to another component of the detector, and
the controller is configured to
receive a signal from the detector,
compare the signal from the detector to a reference signal from the detector, and
when the signal from the detector has a voltage that is less than a corresponding voltage of the reference signal, control the adjustment system associated with the source to execute at least one source adjustment when the detection assembly includes the adjustment system associated with the source and/or control the adjustment system associated with the detector to execute at least one detector adjustment when the detection assembly includes the adjustment system associated with the detector to increase the voltage of the signal from the detector.

11. A fluid processing device, comprising:
a detection assembly including
a source associated with a component of the fluid processing device, provided in an initial position and an initial orientation with respect to said component of the fluid processing device, and configured to emit a signal, and
a detector associated with a structure of the fluid processing device, provided in an initial position and an initial orientation with respect to said structure of the fluid processing device, and configured to receive at least a portion of the signal; and
a controller, wherein
the detection assembly further includes
an adjustment system associated with the source, with the controller being configured to control the adjustment system to execute a source adjustment in which the position and/or the orientation of the source is adjusted with respect to said component of the fluid processing device and/or a position and/or an orientation of a component of the source is adjusted with respect to another component of the source, and/or
an adjustment system associated with the detector, with the controller being configured to control the adjustment system to execute a detector adjustment in which the position and/or the orientation of the detector is adjusted with respect to said structure of the fluid processing device and/or a position and/or an orientation of a component of the detector is adjusted with respect to another component of the detector, and
the fluid processing device is configured to accommodate a fluid flow circuit for conducting fluid flow through the fluid processing device, and
the controller is configured to receive an orientation signal indicative of a position and/or an orientation of a component of a fluid flow circuit associated to the fluid processing device, determine whether the position and/or the orientation of said component of the fluid flow circuit is different from an expected position and/or an expected orientation, and when the position and/or the orientation of said component of the fluid flow circuit is different from the expected position and/or the expected orientation, control the adjustment system associated with the source to execute at least one source adjustment when the detection assembly includes the adjustment system associated with the source and/or control the adjustment system associated with the detector to execute at least one detector adjustment when the detection assembly includes the adjustment system associated with the detector to account for the position and/or the orientation of said component of the fluid flow circuit.

12. A method of monitoring a fluid and/or a fluid component in a fluid processing device including a source and a detector, the source being associated with a component of the fluid processing device and provided in an initial position and an initial orientation with respect to said component of the fluid processing device, and the detector being associated with a structure of the fluid processing device and provided in an initial position and an initial orientation with respect to said structure of the fluid processing device, the method comprising:

emitting a signal from the source and to a fluid and/or a fluid component in the fluid processing device;

receiving at least a portion of the signal with the detector;

executing a plurality of different source adjustments in which the source is moved into a plurality of different positions and/or orientations with respect to said component of the fluid processing device and/or a component of the source is moved into a plurality of different positions and/or orientations with respect to another component of the source and/or executing a plurality of different detector adjustments in which the detector is moved into a plurality of different positions and/or orientations with respect to said structure of the fluid processing device and/or a component of the detector is moved into a plurality of different positions and/or orientations with respect to another component of the detector;

receiving signals from the detector for each of said plurality of different source adjustments and/or detector adjustments;

comparing the signals from the detector to each other to determine the source adjustment and/or detector adjustment in which the signal from the detector has maximum voltage; and executing the source adjustment and/or detector adjustment in which the signal from the detector has maximum voltage.

13. The method of claim 12, wherein the source is stationary while emitting said signal.

14. The method of claim 12, wherein the source is moving while emitting said signal.

15. The method of claim 12, wherein the detector is stationary while receiving said at least a portion of the signal.

16. The method of claim 12, wherein the detector is moving while receiving said at least a portion of the signal.

17. The method of claim 12, wherein the source comprises a light source and the detector comprises a light detector.

18. The method of claim 17, wherein said component of the source comprises a lens.

19. A method of monitoring a fluid and/or a fluid component in a fluid processing device including a source and a detector, the source being associated with a component of the fluid processing device and provided in an initial position and an initial orientation with respect to said component of the fluid processing device, and the detector being associated with a structure of the fluid processing device and provided in an initial position and an initial orientation with respect to said structure of the fluid processing device, the method comprising:

emitting a signal from the source and to a fluid and/or a fluid component in the fluid processing device;

receiving at least a portion of the signal with the detector;

emitting a signal from the detector;

comparing the signal from the detector to a reference signal from the detector; and when the signal from the detector has a voltage that is less than a corresponding voltage of the reference signal, executing a source adjustment in which the position and/or the orientation of the source is adjusted with respect to said component of the fluid processing device and/or the position and/or the orientation of said component of the source is adjusted with respect to said another component of the source and/or executing a detector adjustment in which the position and/or the orientation of the detector is adjusted with respect to said structure of the fluid processing device and/or the position and/or the orientation of said component of the detector is adjusted with respect to said another component of the detector to increase the voltage of the signal from the detector.

20. A method of monitoring a fluid and/or a fluid component in a fluid processing device configured to accommodate a fluid flow circuit for conducting fluid flow through the fluid processing device and including a source and a detector, the source being associated with a component of the fluid processing device and provided in an initial position and an initial orientation with respect to said component of the fluid processing device, and the detector being associated with a structure of the fluid processing device and provided in an initial position and an initial orientation with respect to said structure of the fluid processing device, the method comprising:

emitting a signal from the source and to a fluid and/or a fluid component in the fluid processing device;

receiving at least a portion of the signal with the detector;

determining whether a position and/or an orientation of a component of a fluid flow circuit accommodated by the fluid processing device is different from an expected position and/or an expected orientation; and when the position and/or the orientation of said component of the fluid flow circuit is different from the expected position and/or the expected orientation, executing a source adjustment in which the position and/or the orientation of the source is adjusted with respect to said component of the fluid processing device and/or the position and/or the orientation of said component of the source is adjusted with respect to said another component of the source and/or executing a detector adjustment in which the position and/or the orientation of the detector is adjusted with respect to said structure of the fluid processing device and/or the position and/or the orientation of said component of the detector is adjusted with respect to said another component of the detector to account for the position and/or the orientation of said component of the fluid flow circuit.

* * * * *